United States Patent

Sugiura et al.

[11] Patent Number: 5,977,035
[45] Date of Patent: Nov. 2, 1999

[54] LIQUID AGENT FOR CONTACT LENS CONTAINING CARBOXYLATED AMINE AS A PRESERVATIVE OR STERILIZING COMPONENT

[75] Inventors: Makoto Sugiura, Gifu; Keiko Ibaraki, Nagoya, both of Japan

[73] Assignee: Tomey Technology Corporation, Japan

[21] Appl. No.: 08/917,503

[22] Filed: Aug. 26, 1997

[30] Foreign Application Priority Data

Aug. 30, 1996 [JP] Japan .................................. 8-230176

[51] Int. Cl.$^6$ .................................. C11D 3/48; C11D 1/88
[52] U.S. Cl. ...................... 510/112; 510/383; 510/420; 510/490; 510/840
[58] Field of Search .................... 510/112, 113, 510/114, 115, 382, 383, 420, 490; 514/839, 840; 252/131, 198, 166, 132; 422/28

[56] References Cited

U.S. PATENT DOCUMENTS

| | | | |
|---|---|---|---|
| 4,485,029 | 11/1984 | Kato et al. | 514/544 |
| 4,533,399 | 8/1985 | Menckr | 134/6 |
| 5,035,859 | 7/1991 | Gu et al. | 422/28 |
| 5,314,823 | 5/1994 | Nakagawa | 435/264 |
| 5,422,029 | 6/1995 | Potini et al. | 510/112 |
| 5,500,144 | 3/1996 | Potini et al. | 510/115 |
| 5,604,189 | 2/1997 | Zhang et al. | 510/112 |
| 5,607,908 | 3/1997 | Potini et al. | 510/115 |
| 5,756,139 | 5/1998 | Harvey et al. | 426/298 |
| 5,773,396 | 6/1998 | Zhang et al. | 510/115 |

FOREIGN PATENT DOCUMENTS

| | | |
|---|---|---|
| 52-109953 | 9/1977 | Japan . |
| 62-153217 | 7/1987 | Japan . |
| 63-59960 | 3/1988 | Japan . |
| 95/04126 | 2/1995 | WIPO . |
| 96/06153 | 2/1996 | WIPO . |

*Primary Examiner*—Ardith Hertzog
*Attorney, Agent, or Firm*—Parkhurst & Wendel, L.L.P.

[57] ABSTRACT

A liquid agent for a contact lens containing, as a preservative or sterilizing component, a carboxylated amine represented by the following formula,

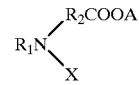

wherein $R_1$ represents an alkyl group having 6–18 carbon atoms, $R_2$ represents an alkylene group having 1–18 carbon atoms, A represents Na, K or H, and X represents H or —$R_3$COOZ group, wherein $R_3$ represents an alkylene group having 1–18 carbon atoms and Z represents Na, K or H.

9 Claims, No Drawings

LIQUID AGENT FOR CONTACT LENS CONTAINING CARBOXYLATED AMINE AS A PRESERVATIVE OR STERILIZING COMPONENT

BACKGROUND OF THE INVENTION

1. Field of the Invention

The present invention relates to a liquid agent for contact lens, which agent is capable of exhibiting an excellent preservative or sterilizing effect while assuring a sufficiently high degree of safety with respect to the eyes of the user.

2. Discussion of the Related Art

The contact lens worn on the eye of the user is likely to be soiled with stains such as proteins and lipids which are included in the tear fluid. These stains adhering to the contact lens not only deteriorate the wearing comfort of the contact lens as felt by the user, but also lower the eyesight of the user and cause various troubles to the eye such as hyperemia of the conjunctiva. Further, microorganisms such as bacteria adhering to the surface of the contact lens may proliferate thereon while the contact lens is stored after it is removed from the eye of the user. Such microorganisms may cause infectious diseases, giving adverse influences on the eye of the user.

In view of the above, the contact lens needs to be treated for cleaning and disinfection on a regular basis for safe and comfortable wearing thereof. In general, the contact lens is treated in the following manner. Initially, the contact lens which was removed from the eye is rubbed with a cleaning agent including a surface active agent, to thereby remove lipid stains deposited on the sufaces of the contact lens. If it is desired to remove protein stains, the contact lens is soaked in a cleaning agent including a proteolytic enzyme so as to remove the protein stains. After the contact lens is rinsed with a rinsing liquid, the contact lens is accommodated and stored in a container filled with a storing liquid. Since the microorganisms tend to adhere to and proliferate on the lens surfaces, especially where the contact lens is a water-containing or hydrogel lens, such water-containing or hydrogel contact lens needs to be disinfected by boiling. Namely, the hydrogel contact lens accommodated in a container requires a boiling procedure using a suitable boiling apparatus, in addition to the above-described procedure.

Thus, the procedure for treating the contact lenses is cumbersome, requiring several kinds of liquid agents such as a cleaning liquid and storing liquid, and a suitable apparatus for boiling the contact lenses. Accordingly, it is troublesome and costly for the contact lens users to treat the contact lenses.

For solving the above-described problem, there are proposed some methods for treating the contact lens in a simplified manner at a relatively low cost. These methods permit the contact lens to be treated by using a single liquid agent which is obtained by adding, to the storing liquid, a surface active agent, a protein removing agent, and a disinfectant. In these proposed methods, the contact lens is disinfected not by a thermal disinfecting method which requires the above-described boiling apparatus, but by a chemical disinfecting method using a disinfectant. Thus, the proposed methods eliminate the conventionally required boiling operation using the exclusive apparatus for boiling the contact lens, so as to facilitate the procedure for treating the contact lens.

The above-described contact lens liquid agent functions not only as a disinfectant which has a chemical disinfecting effect, but also as a storing liquid. Such a contact lens liquid agent is required to exhibit a high degree of sterilizing effect, and at the same time, a low degree of toxicity with respect to the eyes, since the contact lens is soaked in the liquid agent for a relatively long period of time.

As the disinfectant used in commercially available chemical disinfecting agents for the contact lens, thimerosal, chlorhexidine or quaternary ammonium salt (e.g., benzalkonium chloride) is used. In JP-A-52-109953, JP-A-62-153217 and JP-A-63-59960, there are proposed a disinfectant or liquid agent for contact lenses, which includes benzalkonium chloride in an amount of 0.001–0.2%, and a disinfectant for soft contact lenses, which includes chlorhexidine in an amount of 0.01–0.05%.

However, it is reported that such a disinfectant functions as an allergy intensifier and harms to the eyes of the user. Further, the disinfectant is adsorbed on or stored in the contact lens over a long period of use. For example, corneal troubles may be caused due to emission of the highly condensed disinfectant from the contact lens to the eye during wearing of the contact lens, or due to direct contact of the eye with the contact lens on which the disinfectant is adsorbed with high concentration ("Journal of Japan Contact Lens Society" 34:267–276, 277–282, 1992, 35:219–225, 1993, 36:57–61, 1994, 37:35–39, 154–157, 1995).

In an attempt to avoid such troubles, it may be considered to lower the concentration of the disinfectant to be used, for assuring a high degree of safety with respect to the eyes. In this case, however, the sterilizing action of the disinfectant is inevitably lowered, so that the contact lens may become contaminated with the microorganisms.

SUMMARY OF THE INVENTION

It is therefore an object of the present invention to provide a liquid agent for a contact lens which can be used with a high degree of safety, and which exhibits a sufficiently high sterilizing effect with considerably reduced toxicity to the eyes.

As a result of an extensive study about the disinfectant used in the liquid agent for a contact lens, the inventors of the present invention have found that a certain carboxylated amine conventionally known as a shampoo base has a sufficiently high degree of safety with low toxicity to the eyes, and can be used as a preservative or sterilizing component in the liquid agent for the contact lens. Further the study made by the inventors revealed that the contact lens liquid agent that contains the carboxylated amine as the preservative or disinfecting agent exhibits a sufficiently high degree of sterilizing effect and safety suitable for practical use.

The above object of the present invention may be attained according to the principle of the present invention which provides a liquid agent for a contact lens containing, as a preservative or sterilizing component, a carboxylated amine represented by the following formula,

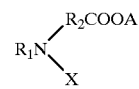

wherein $R_1$ represents an alkyl group having 6–18 carbon atoms, $R_2$ represents an alkylene group having 1–18 carbon atoms, A represents Na, K or H, and X represents H or —$R_3$COOZ group, wherein $R_3$ represents an alkylene group having 1–18 carbon atoms and Z represents Na, K or H.

In the liquid agent for the contact lens according to the present invention, the carboxylated amine is contained as the preservative or sterilizing component. Thus, the present liquid agent for the contact lens exhibits a sterilizing action over a wide range of antibacterial spectrum. In addition, the present contact lens liquid agent has considerably reduced toxicity with respect to the eyes, so that it does not give an adverse influence on the cornea of the eye of the user. Accordingly, the contact lens liquid agent of the present invention exhibits excellent preservative and sterilizing effect and assures a high degree of safety.

Since the carboxylated amine is an amphoteric surface active agent, it permits the addition of the other disinfectant and a surface active agent as a cleaning component to the contact lens liquid agent, without adversely influencing the effects to be exhibited by the disinfectant and the surface active agent, irrespective of the kinds of the disinfectant to be added and irrespective of whether the surface active agent to be added is anionic, nonionic or cationic. Accordingly, the present contact lens liquid agent permits a considerably high degree of freedom in selecting the disinfectant and surface active agent to be added thereto.

In a first preferred form of the present invention, the carboxylated amine is present in a concentration in a range between not lower than 0.01 ppm and less than 500 ppm. According to this arrangement, the liquid agent for the contact lens of the present invention exhibits a sufficiently high degree of sterilizing effect even at a relatively low concentration. Thus, the present contact lens liquid agent can be used at a low concentration, so as to minimize the influence on the living body.

In a second preferred form of the present invention, a pH of the liquid agent, which represents a hydrogen ion concentration in the liquid agent, is in a range of 5.0–9.0. For the purpose of stably keeping the hydrogen ion concentration of the contact lens liquid agent within the above-described range, the contact lens liquid agent further contains a borate buffer. The inclusion of the borate buffer improves the stability of the hydrogen ion concentration (pH) of the contact lens liquid agent. In addition, owing to the inclusion of the borate buffer, the contact lens liquid agent exhibits a higher degree of sterilizing effect especially when the concentration of the carboxylated amine contained therein is relatively low, than a contact lens liquid agent which does not include the borate buffer. Thus, the present contact lens liquid agent assures further enhanced safety.

DETAILED DESCRIPTION OF THE PREFERRED EMBODIMENT

In the present invention, the carboxylated amine which has an excellent sterilizing or disinfecting effect and a high degree of safety with respect to the user's eyes, and which has the predetermined structure represented by the above formula, is used as a preservative or sterilizing component in a liquid agent for a contact lens. It is an object of the present invention to provide such a liquid agent for a contact lens which permits the contact lens to be easily treated for cleaning and disinfection.

The carboxylated amine used in the contact lens liquid agent of the present invention and represented by the above formula has been conventionally used as a base of a weak acid shampoo, conditioning shampoo and cationic shampoo, or as a foaming agent of an aerosol and cleansing cream. In the above formula which represents the carboxylated amine used in the present invention, $R_1$ is an alkyl group having 6–18, preferably 8–12 carbon atoms, $R_2$ is an alkylene group having 1–18, preferably 2–8 carbon atoms, A is selected from among Na, H and K, and X represents H or $-R_3COOZ$ group, wherein $R_3$ is an alkylene group having 1–18, preferably 2–8 carbon atoms and Z is selected from among Na, K and H. The thus specified carboxylated amine is favorably used as a sterilizing component of the contact lens liquid agent of the present invention.

One example of the carboxylated amine is laurylaminopropionic acid which is represented by the above formula, wherein $R_1$ is an alkyl group having 12 carbon atoms, $R_2$ is an alkylene group having 2 carbon atoms, A is H and Z is H. Another example of the carboxylated amine is sodium laurylaminodipropionate which is represented by the above formula, wherein $R_1$ is an alkyl group having 12 carbon atoms, $R_2$ and $R_3$ are an alkylene group having 2 carbon atoms, A is H and Z is Na. Other examples of the carboxylated amine are octylaminopropionic acid, sodium octylaminodipropionate, 2-octylaminopropionic acid, sodium 2-octylaminodipropionate, nonylaminopropionic acid, sodium nonylaminodipropionate, decylaminopropionic acid, sodium decylaminodipropionate, undecylaminopropionic acid and sodium undecylaminodipropionate. In the present invention, any one of, or any combination of these carboxylated amines may be used.

Among these carboxylated amines, the laurylaminopropionic acid is particularly preferred. Products which contain the laurylaminopropionic acid are commercially available. For instance, "Dariphat 151C" is commercially available from Henkel Hakusui Co. Ltd., Japan, as a shampoo base. This product is listed on the Japan Cosmetic Ingredients Dictionary (JCID) IV-407, and assures a high degree of safety. The present invention suitably utilizes such a product.

The carboxylated amine exhibits a desired effect when its concentration is in a range between not lower than 0.01 ppm and less than 500 ppm. In particular, the carboxylated amine exhibits an excellent preservative or sterilizing effect when its concentration is in a range of 0.01 ppm–100 ppm. If the concentration of the carboxylated amine is lower than 0.01 ppm, it is difficult to obtain the desired preservative and sterilizing effect. On the other hand, the concentration of the carboxylated amine exceeding the upper limit of 500 ppm may give an adverse influence on the living body.

The pH of the present contact lens liquid agent is suitably within a range of 5.0–9.0. The pH outside this range may cause irritation to the eye tissue, leading to undesirable troubles of the eyes.

To keep the pH of the contact lens liquid agent within the above-described range for assuring safety with respect to the eyes, at least one buffer is added to the contact lens liquid agent. The buffer is suitably selected from among any known buffers such as borate buffer, phosphate buffer, tris buffer and citrate buffer. The borate buffer is particularly preferable since the contact lens liquid agent used in combination with the borate buffer assures a desired sterilizing effect even if the concentration of the carboxylated amine is relatively low. The buffer is contained in the contact lens liquid agent generally in an amount of 0.05–3.0 w/v %, preferably in an amount of 0.1–1.5 w/v %. If the concentration of the buffer is lower than 0.05 w/v %, it is difficult to keep the pH of the contact lens liquid agent at a constant level. On the other hand, the concentration of the buffer exceeding the above upper limit of 3.0 w/v % does not significantly increase the stability of the pH.

The contact lens liquid agent may further contain a suitable surface active agent for removing stains such as lipid adhering to the contact lens. Any known surface active agents may be employed provided that they assure a high degree of safety with respect to the living body without adversely influencing the material of the contact lens. Since the carboxylated amine as the sterilizing component is an amphoteric material, the surface active agent to be contained in the present contact lens liquid agent may be any one of anionic, cationic, amphoteric and nonionic.

For obtaining a higher degree of sterilizing effect, the present contact lens liquid agent may be used in combination with other disinfectants. Examples of the disinfectant which can be used with the carboxylated amine are a guanidine disinfectant, a quaternary ammonium salt disinfectant and a thiazoline disinfectant which function also as a cationic surface active agent, and a glycine disinfectant which functions also as an amphoteric surface active agent. If the contact lens liquid agent is used in combination with any one of these disinfectants, the sterilizing effect to be exhibited by each of the disinfectants is synergistically increased, to thereby assure a higher degree of sterilizing effect than a contact lens liquid agent which employs only the carboxylated amine as the sterilizing component.

The contact lens liquid agent of the present invention may contain, as needed, any known additional components such as a chelating agent, thickener, tonicity agent and protein removing agent, as long as they assure safety with respect to the living body without giving an adverse influence on the material of the contact lens. Each of these additional components is contained in the present contact lens liquid agent in an amount that does not interfere the sterilizing effect to be exhibited by the carboxylated amine. As the chelating agent, sodium edetate or trihydroxymethylaminomethane is used, for example. As the thickener, propylene glycol, hydroxymethylcellulose, polyvinyl pyrrolidone or polysaccharide is used, for example. When the present contact lens liquid agent is used as a rinsing liquid or a storing liquid, the tonicity agent is preferably included therein so as to reduce irritation to the eye tissue. In this case, the osmotic pressure of the contact lens liquid agent is adjusted to generally 150–400 mOsm, preferably 200–350 mOsm. Examples of the tonicity agent are sodium chloride, potassium chloride and sodium bicarbonate. For enabling the contact lens liquid agent to exhibit the cleaning effect with respect to protein stains, a suitable protein removing agent (i.e., proteolytic enzyme) such as cerine protease, thiol protease, metal protease or carboxyl protease may be included therein.

The present contact lens liquid agent is easily prepared in a way as usually used for preparing an aqueous solution, without requiring any special procedure. Namely, the present contact lens liquid agent containing the carboxylated amine is obtained by dissolving each component in a predetermined amount of sterilized purified water. The obtained contact lens liquid agent (aqueous solution) is clear, and is subjected to sterile filtration, as needed.

The contact lens is treated for cleaning and disinfection by using the contact lens liquid agent prepared as described above, in the following manner. Initially, several droplets of the contact lens liquid agent are applied to a contact lens which was removed from the eye. Then, the contact lens is cleaned by rubbing for several tens of seconds while the contact lens is held by and between a thumb and a forefinger or the contact lens is placed on a palm. After the contact lens is rinsed with the present contact lens liquid agent, it is accommodated in a container filled with the contact lens liquid agent. The contact lens is soaked in the contact lens liquid agent for disinfection for a time period of from 10 minutes to 24 hours, preferably for a time period of from 30 minutes to 4 hours. It is to be understood that the contact lens may be otherwise treated using the contact lens liquid agent of the present invention.

According to a series of procedures as described above, the contact lens can be effectively and easily disinfected without using the conventionally required boiling apparatus. Since the carboxylated amine as the sterilizing component assures a high degree of safety with respect to the eyes, the contact lens can be disinfected safely without causing any troubles to the eyes even when the contact lens is soaked in the contact lens liquid agent for a relatively long period of time.

EXAMPLES

To further clarify the concept of the present invention, some examples of the invention will be described. It is to be understood that the invention is not limited to the details of the illustrated examples, but may be embodied with various changes, modifications and improvements, which may occur to those skilled in the art without departing from the scope of the invention defined in the attached claims.

EXAMPLE 1

Test for checking the sterilizing effect: the influence of pH

As the test bacteria, *Pseudomonas aeruginosa* ATCC 9027 (P.a.) was used. After the P.a. was cultured by using soybean-casein medium at 35° C. for 24 hours, it was suspended with a physiological salt solution or saline, so as to provide a bacteria suspension (bacteria liquid) of $10^8$ cfu/mL.

Specimens Nos. 1–3 of the contact lens liquid agent according to the present invention were prepared so as to have respective compositions as indicated in TABLE 1. As comparative examples, there were prepared specimens Nos. 1–3 of the contact lens liquid agent so as to have respective compositions as also indicated in TABLE 1. The pH of each specimen was adjusted. The specimens of the contact lens liquid agent were respectively poured into sterilized test tubes in an amount of 10 mL. To each of the test tubes, 0.05 mL of the bacteria suspension prepared as described above was added. Each of the thus obtained mixtures was stored in a thermostat kept at 23° C. A predetermined amount of the mixture was taken out of each of the test tubes 4 hours after the preparation of the mixture and 24 hours after the preparation of the mixture, respectively. Each of the mixtures was diluted with sterilized physiological salt solution or saline, and was measured of its viable cell count by the poured plate method. In the poured plate method, each of the mixtures was cultured by using the soybean-casein medium at 35° C. for 3 days.

On the basis of the viable cell count immediately after the inoculation of each mixture and the viable cell count 4 hours after the preparation of each mixture, there was calculated a rate of reduction of the bacteria. Similarly, on the basis of the viable cell count immediately after the inoculation of each mixture and the viable cell count 24 hours after the preparation of each mixture, there was calculated a rate of reduction of the bacteria. The results are shown in TABLE 1. In the following Examples, "Dariphat 151C" (available from Henkel Hakusui Co. Ltd., Japan) is used as the laurylaminopropionic acid.

TABLE 1

|  | Present invention | | | Comparative examples | | |
|---|---|---|---|---|---|---|
|  | 1 | 2 | 3 | 1 | 2 | 3 |
| laurylaminopropionic acid (ppm) | 10 | 10 | 10 | — | — | — |
| sodium dihydrogenphosphate dihydrate (%) | 1.22 | 0.487 | 0.066 | 1.22 | 0.487 | 0.066 |
| disodium hydrogenphosphate (%) | 0.022 | 0.678 | 1.053 | 0.022 | 0.678 | 1.053 |
| sodium chloride (%) | 0.45 | 0.38 | 0.34 | 0.45 | 0.38 | 0.34 |
| pH | 5 | 7 | 8 | 5 | 7 | 8 |
| reduction rate after 4 hours (%) | 99.7 | 99.8 | 100 | 31.6 | 21.1 | 54.2 |
| after 24 hours (%) | 100 | 100 | 100 | 78.4 | * | * |

*: increase

It will be understood from the above results that the contact lens liquid agent specimens Nos. 1–3 according to the present invention exhibit a higher degree of sterilizing effect, regardless of its pH values, than the contact lens liquid agent specimens Nos. 1–3 according to the Comparative examples.

EXAMPLE 2

Test for checking the inhibitory effect on proliferation of bacteria: the influence of combined use with other disinfectant The inhibitory effect on proliferation of bacteria was examined when the carboxylated amine was used in combination with other disinfectant.

According to the MIC measuring method of the JAPAN SOCIETY OF CHEMOTHERAPY, the proliferation of bacteria was inspected. Two kinds of bacteria suspension were obtained in the following manner. Namely, after the P.a. and *Staphylococcus aureus* ATCC 6538 (S.a.) were respectively cultured by using the soybean-casein medium at 35° C. for 24 hours, they were suspended with the physiological salt solution, so as to provide the respective bacteria suspensions of $10^7$ cfu/mL.

There were prepared two kinds of test solutions, one of which includes the laurylaminopropionic acid (the carboxylated amine) and a hexadecyltrimethyl ammonium salt (the quaternary ammonium salt disinfectant) in different amounts as indicated in the following TABLES 2 and 4, and the other of which includes the laurylaminopropionic acid (the carboxylated amine) and an alkylaminoethylglycine hydrochloride (the glycine disinfectant) in different amounts as indicated in the following TABLES 3 and 5. Each of the test solutions was prepared by using Müller-Hinton medium. To 1 mL of the test solutions, 0.01 mL of the bacteria suspensions prepared as described above were respectively added. The test solutions were inspected for the proliferation of the bacteria after they were cultured at 35° C. for 24 hours. The following TABLES 2 and 3 show the inhibitory effect on the proliferation of the P.a., while TABLES 4 and 5 show the inhibitory effect on the proliferation of S.a. The test solutions were evaluated for the inhibitory effect on the proliferation of the P.a. and S.a. as indicated below:

+++: Considerable turbidity due to the proliferation of the bacteria (P.a. or S.a.) was observed.
++: Turbidity due to the proliferation of the bacteria (P.a. or S.a.) was observed.
+: Slight turbidity due to the proliferation of the bacteria (P.a. or S.a.) was observed.
−: No proliferation of the bacteria (P.a. or S.a.) was observed.

In this Example 2, "Dariphat 151C" (available from Henkel Hakusui Co. Ltd., Japan) was used as the laurylaminopropionic acid, "PB-300" (available from Nippon Oil and Fats Co. Ltd., Japan) was used as the hexadecyltrimethyl ammonium salt, and "TEGO-51" (available from Nihon Shoji Co. Ltd., Japan) was used as the alkylaminoethylglycine hydrochloride.

TABLE 2

|  | 1 | 2 | 3 | 4 | 5 |
|---|---|---|---|---|---|
| laurylaminopropionic acid (ppm) | 31.3 | 31.3 | 31.3 | 0 | 0 |
| hexadecyltrimethyl ammonium salt (ppm) | 0 | 3.12 | 6.25 | 3.12 | 6.25 |
| proliferation of the bacteria (P.a.) | + | − | − | +++ | +++ |

TABLE 3

|  | 1 | 2 | 3 | 4 | 5 |
|---|---|---|---|---|---|
| laurylaminopropionic acid (ppm) | 31.3 | 31.3 | 15.6 | 0 | 0 |
| alkylaminoethylglycine hydrochloride (ppm) | 0 | 12.5 | 25.0 | 12.5 | 25.0 |
| proliferation of the bacteria (P.a.) | + | − | − | +++ | ++ |

TABLE 4

|  | 1 | 2 | 3 | 4 | 5 |
|---|---|---|---|---|---|
| laurylaminopropionic acid (ppm) | 7.80 | 3.90 | 3.90 | 0 | 0 |
| hexadecyltrimethyl ammonium salt (ppm) | 0 | 0 | 0.78 | 0.39 | 0.78 |
| proliferation of the bacteria (S.a.) | + | − | − | +++ | +++ |

TABLE 5

|  | 1 | 2 | 3 | 4 | 5 |
|---|---|---|---|---|---|
| laurylaminopropionic acid (ppm) | 7.80 | 7.80 | 3.90 | 0 | 0 |
| alkylaminoethylglycine hydrochloride (ppm) | 0 | 3.12 | 6.25 | 3.12 | 6.25 |
| proliferation of the bacteria (S.a.) | + | − | − | +++ | ++ |

As is apparent from the above results, it was confirmed that the test solutions of the present invention in which the carboxylated amine is used in combination with the other disinfectant completely inhibited the proliferation of the bacteria, or delayed or restrained the proliferation of the bacteria, in contrast with the test solutions of the Comparative examples in which only one of the carboxylated amine and the other disinfectant is used.

EXAMPLE 3

Test for checking the sterilizing effect: the influence of a buffer

Initially, there were prepared a borate buffer (BBS) and a tris buffer (TRIS) having respective compositions as indicated below. By using the thus prepared two buffers (BBS and TRIS) and purified water (NBS), there were prepared various contact lens liquid agents including the laurylaminopropionic acid in concentrations of 100 ppm, 50 ppm, 25 ppm, 12.5 ppm and 0 ppm, respectively. Each of the contact lens liquid agents was examined of its sterilizing effect.

| [composition of the borate buffer] | |
|---|---|
| boric acid | 0.64% |
| borate | 0.47% |
| sodium chloride | 0.49% |
| [composition of the tris buffer] | |
| 2-amino-2-hydroxymethyl-1,3-propanediol | 0.061% |
| sodium chloride | 0.59% |
| hydrochloric acid | as needed |

As the test bacteria or fungi, the S.a., *Serratia marcescens* ATCC 13880 (S.m.) and *Candida albicans* ATCC 10231 (C.a.) were used. The S.a. was cultured by using the soybean-casein medium at 35° C. for 24 hours. The S.m. was cultured by using the soybean-casein medium at 30° C. for 24 hours. The C.a. was cultured by using Glucose-Peptone medium at 23° C. for 48 hours. Each of the thus cultured S.a., S.m. and C.a. was suspended with the physiological salt solution, so as to provide a bacteria or fungi suspension of $10^6$–$10^7$ cfu/mL.

The contact lens liquid agents having the above-described different concentrations of the laurylamino propionic acid were diluted in two steps with the borate buffer and the tris buffer, respectively, so as to provide test solutions. To 1 mL of each of the test solutions, 0.01 mL of the bacteria suspensions and the fungi suspension were respectively added. The thus obtained mixtures were stored in an incubator kept at 23° C., so that the amount of the bacteria or fungi was $10^5$–$10^6$ cfu/mL. 4 hours later, a predetermined amount of each of the mixtures was taken out of the incubator, and the viable cell count was examined according to plate coating method. In this method, the soybean-casein medium was used, and the S.a. was cultured at 35° C. for 3 days, the S.m. was cultured at 30° C. for 3 days, and the C.a. was cultured at 23° C. for 5 days. The proliferation of the bacteria and fungi after culture was inspected. The degree of proliferation of the bacteria and fungi was evaluated as indicated below. The following TABLES 6, 7 and 8 show the results of the evaluation for the degrees of proliferation of the S.a., S.m., and C.a., respectively.

++++: more than $10^4$ cfu/mL
++ : $10^3$–$10^4$ cfu/mL
++: $10^2$–$10^3$ cfu/mL
+: $10$–$10^2$ cfu/mL
−: less than 10 cfu/mL

TABLE 6

| | Concentration of laurylaminopropionic acid (ppm) | | | | |
|---|---|---|---|---|---|
| buffer | 100 | 50 | 25 | 12.5 | 0 |
| BBS | − | − | − | + | ++++ |
| TRIS | − | − | + | + | ++++ |
| NBS | − | + | ++ | ++ | ++++ |

TABLE 7

| | Concentration of laurylaminopropionic acid (ppm) | | | | |
|---|---|---|---|---|---|
| buffer | 100 | 50 | 25 | 12.5 | 0 |
| BBS | − | − | − | − | ++++ |
| TRIS | − | − | + | + | ++++ |
| NBS | + | + | ++ | ++ | ++++ |

TABLE 8

| | Concentration of laurylaminopropionic acid (ppm) | | | | |
|---|---|---|---|---|---|
| buffer | 100 | 50 | 25 | 12.5 | 0 |
| BBS | − | − | − | − | ++++ |
| TRIS | − | − | + | + | ++++ |
| NBS | − | + | ++ | ++ | ++++ |

As is apparent from the above results, the contact lens liquid agent containing the buffer, in particular, the borate buffer, exhibited a sufficiently high degree of sterilizing effect.

EXAMPLE 4

Test for checking the sterilizing effect: the effect on fungi

As the test fungi, *Aspergillus niger* ATCC 16404 (A.n.) and the C.a. were used. After the A.n. was cultured by using the Glucose-Peptone medium at 23° C. for 7 days, it was suspended with a physiological salt solution including 0.05% of Polysorbate 80. The obtained suspension was filtered through sterilized polypropylene cotton, so as to provide a spore suspension. This spore suspension was adjusted to $10^8$ cfu/mL to provide a fungi liquid. The C.a. was treated as in the above Example 3, so as to provide a fungi liquid of $10^8$ cfu/mL.

Specimens Nos. 4 and 5 of the contact lens liquid agent according to the present invention and specimen No. 4 of the contact lens liquid agent according to the comparative example were prepared so as to have respective compositions as indicated in the following TABLE 9. Further, chemical disinfectants for contact lenses (as shown in TABLE 10) commercially available from other companies were prepared as specimens Nos. 5–7 of the contact lens liquid agent according to the comparative example.

TABLE 9

|  | Present invention | | Comparative example |
| --- | --- | --- | --- |
|  | 4 | 5 | 4 |
| laurylaminopropionic acid (ppm) | 10 | 25 | — |
| boric acid (%) | 0.64 | 0.64 | 0.64 |
| borate (%) | 0.47 | 0.47 | 0.47 |
| sodium chloride (%) | 0.49 | 0.49 | 0.49 |

TABLE 10

| Comparative examples | Manufacturer | Disinfectant | Concentration of the disinfectant (ppm) |
| --- | --- | --- | --- |
| 5 | Company A | polyhexamethylene biguanide | 0.5 |
| 6 | Company B | polyquaternium-1 | 11 |
| 7 | Company C | chlorhexidine gluconate | 10 |

As in the above Example 1, various mixtures of the specimens of the contact lens liquid agent and the fungi liquids prepared as described above were obtained. The obtained mixtures were stored in the thermostat kept at 23° C. In the same manner as in the above Example 1, the viable cell counts were measured for a predetermined amount of each of the mixtures 2 hours after the preparation of the mixture and 4 hours after the preparation of the mixture, respectively. The mixtures were cultured by using the Glucose-Peptone medium at 23° C. for 5 days.

On the basis of the viable cell count immediately after the inoculation of each mixture and the viable cell count 2 hours after the preparation of each mixture, there was calculated a rate of reduction of the fungi. Similarly, on the basis of the viable cell count immediately after the inoculation of each mixture and the viable cell count 4 hours after the preparation of each mixture, there was calculated a rate of reduction of the fungi. The results are shown in TABLE 11.

TABLE 11

|  | reduction rate of A.n. (%) | | reduction rate of C.a. (%) | |
| --- | --- | --- | --- | --- |
|  | after 2 hours | after 4 hours | after 2 hours | after 4 hours |
| Present Invention | | | | |
| 4 | >99.9 | 100 | >99.9 | >99.9 |
| 5 | 100 | 100 | >99.9 | 100 |
| Comparative examples | | | | |
| 4 | — | increase | 29.5 | 34.4 |
| 5 | — | increase | — | 99.8 |
| 6 | — | increase | — | 37.3 |
| 7 | — | 0.35 | — | 66.7 |

—: not calculated

As is apparent from the above results, the contact lens liquid agent specimens Nos. 4–5 according to the present invention exhibited a considerably higher degree of sterilizing effect than the chemical disinfectants for the contact lenses (specimens Nos. 5–7 according to the comparative examples) commercially available from the other companies.

EXAMPLE 5

Test for checking the sterilizing effect: the influence of a borate buffer when the concentration of the carboxylated amine is low Specimens Nos. 6–8 of the contact lens liquid agent according to the present invention and specimen No. 8 of the contact lens liquid agent according to a comparative example were prepared so as to have respective compositions as indicated in the following TABLE 12. As in the above Example 1, these specimens of the contact lens liquid agent were examined for the sterilizing effect by using the P.a. On the basis of the viable cell count immediately after the inoculation of the mixture of each specimen and the bacteria (P.a.) suspension and the viable cell count 4 hours after the preparation of the mixture, the reduction rate of the P.a. was calculated. Similarly, on the basis of the viable cell count immediately after the inoculation of the mixture and 24 hours after the preparation of the mixture, the reduction rate of the P.a. was calculated. The results are also shown in TABLE 12.

TABLE 12

|  | Present invention | | | Comparative example |
| --- | --- | --- | --- | --- |
|  | 6 | 7 | 8 | 8 |
| laurylaminopropionic acid (ppm) | 10 | 5 | 1 | — |
| boric acid (%) | 0.64 | 0.64 | 0.64 | 0.64 |
| borate (%) | 0.47 | 0.47 | 0.47 | 0.47 |
| sodium chloride (%) | 0.49 | 0.49 | 0.49 | 0.49 |
| reduction rate | | | | |
| after 4 hours (%) | 100 | >99.9 | 59.3 | — |
| after 24 hours (%) | 100 | 100 | 99.6 | 83.6 |

As is apparent from the above results, when the contact lens liquid agent according to the present invention contains the borate buffer, it is capable of exhibiting a significantly enhanced sterilizing effect even if the concentration of the carboxylated amine is relatively low.

EXAMPLE 6

Cell toxicity test: the influence on soft contact lenses

The present contact lens liquid agent was evaluated in terms of safety, by effecting the cell toxicity test in the following manner.

As the test solutions, there were prepared specimens Nos. 6–7 of the contact lens liquid agent according to the present invention (as used in the above Example 5), and a specimen No. 9 according to a comparative example which is a 0.05% aqueous solution of chlorhexidine. In 2.0 mL of each test solution, soft contact lens ("MENICON SOFT 72" available from Menicon Co. Ltd., Japan) were immersed for 18 hours, so as to provide sample lenses.

L-929 cells which had been cultured in a $CO_2$ incubator kept at 37° C. for 3 days were peeled off from a flask by using a trypsin/EDTA solution. The cells were used to prepare a cell suspension of about $2 \times 10^5$ cell/mL, using EAGLE'S MEM medium. 4.5 mL of the obtained cell suspension was inoculated in a Petri dish having a size of 60 mm×15 mm, and was cultured again in the $CO_2$ incubator kept at 37° C. for 48 hours. After removal of the old medium, 4.5 mL of Agar medium was poured. After the Agar medium was hardened, there was added a Neutral Red solution. Then, the cell suspension was cultured in the $CO_2$ incubator kept at 37° C. for one hour. After redundant Neutral Red solution was discarded, each sample lens was placed thereon. In this state, the cell suspension was cultured in the $CO_2$ incubator kept at 37° C. for 48 hours. The cell suspension was evaluated for the toxicity under the influence of the contact lenses liquid agent in which each sample lens was immersed, in the following manner.

The toxicity was evaluated by observing a size of a discolored zone produced by killed cells, and a degree of melting of the cells located right under the contact lens. Described in detail, the size of the discolored zone was visually inspected while the degree of melting of the cells was observed by an inverted microscope. The criteria of the evaluation is indicated in TABLE 13 and the results of the observation are indicated in TABLE 14.

TABLE 13

| size of discolored zone | evaluation | degree of melting | evaluation |
|---|---|---|---|
| none | 0 | none | 0 |
| 0–0.5 mm | 1 | less than 20% | 1 |
| 0.5–1.5 mm | 2 | 20–40% | 2 |
| more than 1.5 mm | 3 | 40–60% | 3 |
|  |  | 60–80% | 4 |
|  |  | more than 80% | 5 |

TABLE 14

|  | Present invention | | Comparative example |
|---|---|---|---|
|  | 6 | 7 | 9 |
| size of discolored zone | 0 | 0 | 3 |
| degree of melting | 0 | 0 | 5 |

In the contact lens liquid agent specimens Nos. 6 and 7 according to the present invention, neither the discolored zone due to the killed cells nor the melting of the cells was not observed. Thus, it was confirmed that the present contact lens liquid agent is not toxic to the cells, assuring a high degree of safety with respect to the eyes. In contrast, it was recognized that the conventionally used disinfectant such as chlorhexidine used in the specimen No. 9 according to the comparative example is toxic to the cells. Thus, the conventionally used disinfectant does not always assure a high degree of safety to the eyes.

EXAMPLE 7

Test for checking the cleaning effect

Specimens Nos. 9 and 10 of the contact lens liquid agent according to the present invention were prepared so as to have respective compositions as indicated in TABLE 15. These specimens were examined for the cleaning effect in the following manner. In TABLE 15, 2-alkyl-N-carboxymethyl-N-hydroxyethylimidazolinium betaine is an amphoteric surface active agent.

Initially, a solution of an artificial lipid to be used in the test was prepared in the following manner. There were dissolved 6 w/v % of sorbitan monooleate, 16 w/v % of castor oil, 35 w/v % of lanolin, 5 w/v % of oleic acid, 4 w/v % of sorbitan trioleate, 2 w/v % of cetyl alcohol, 2 w/v % of cholesterol and 30 w/v % of cholesterol acetate. The obtained solution was agitated so as to provide a homogeneous liquid of an artificial lipid. 2.5 parts of the obtained artificial lipid liquid were mixed with 97.5 parts of a physiological salt solution, to thereby provide the solution of the artificial lipid.

As sample contact lenses, hard contact lenses ("MENICON SUPER EX" available from Menicon Co. Ltd., Japan) were prepared. 5 µL of the artificial lipid solution prepared as described above was uniformly applied to the both surfaces of each contact lens. Thus, the surfaces of each contact lens were soiled with the artificial lipid stain. To one surface of each contact lens which is placed on the palm, there were applied three droplets of each of the contact lens liquid agent specimens Nos. 9 and 10 (namely, six droplets of the contact liquid agent were applied to one contact lens). The contact lenses were cleaned by finger-rubbing for 5 seconds.

TABLE 15

|  | Present invention | |
|---|---|---|
|  | 9 | 10 |
| laurylaminopropionic acid (ppm) | 10 | 10 |
| boric acid (%) | 0.64 | — |
| borate (%) | 0.47 | — |
| sodium chloride (%) | 0.049 | — |
| 2-alkyl-N-carboxymethyl-N-hydroxyethylimidazolinium betaine (%) | — | 0.05 |

The appearance of the contact lenses was observed after each contact lens was cleaned. It was confirmed that the artificial lipid stains adhering to the contact lenses were completely removed therefrom. As is apparent from the results, the contact lens liquid agent according to the present invention exhibits excellent cleaning effect as well as excellent sterilizing effect.

The results of the above Examples indicate that the contact lens liquid agent containing the carboxylated amine according to the present invention is superior over the contact lens liquid agent containing the conventional disinfectant, in terms of safety and sterilizing effect.

It will be clear from the above description that the present contact lens liquid agent which includes the carboxylated amine as the sterilizing component is capable of exhibiting a significantly higher degree of sterilizing effect even if the concentration of the disinfectant is relatively low, as compared with a contact lens liquid agent using the other disinfectant. Thus, the present contact lens liquid agent assures excellent sterilizing effect. Further, the contact lens liquid agent of the present invention assures a higher degree of safety with respect to the eyes than a conventional contact lens liquid agent. The present contact lens liquid agent assures safety and excellent cleaning effect as described above, so that it can be used for cleaning, disinfecting, rinsing and storing the soft contact lenses and hard contact lenses. For disinfection of the contact lenses, the present contact lens liquid agent employs the chemical disinfecting method, eliminating the use of exclusive apparatus for disinfecting the contact lenses such as a boiling apparatus. Thus, the present contact lens liquid agent can simplify the procedure required for treating the contact lenses, assuring easy handling of the contact lenses by the users.

Since the carboxylated amine used in the present contact lens liquid agent is amphoteric, it can be used in combination with any surface active agent such as amphoteric, anionic, nonionic and cationic, and other disinfectants, assuring a high degree of freedom in selecting the surface active agent and disinfectant which are used in combination. When the contact lens liquid agent is used in combination with the other disinfectant, it exhibits a considerably high sterilizing effect owing to a synergetic effect offered by the combined use with the other disinfectant.

What is claimed is:

1. A liquid agent for a contact lens containing:
   a carboxylated amine as a preservative or sterilizing component in a concentration in a range of 0.01 to 50 ppm; and
   a borate buffer in an amount of 0.05 to 3.0 w/v %,
   said carboxylated amine being represented by the following formula,

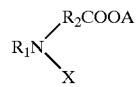

wherein $R_1$ represent an alkyl group having 6–18 carbon atoms, $R_2$ represents an alkylene group having 1–18 carbon atoms, A represents Na, K or H, and X represents H or $-R_3COOZ$ group, wherein $R_3$ represents an alkylene group having 1–18 carbon atoms and Z represents Na, K or H.

2. A liquid agent for a contact lens according to claim 1, wherein said carboxylated amine is present in a concentration in a range of 0.01–10 ppm.

3. A liquid agent for a contact lens according to claim 1, wherein said carboxylated amine is present in a concentration in a range of 0.01–7.8 ppm.

4. A liquid agent for a contact lens according to claim 1, wherein said borate buffer is contained in an amount of 0.1–1.5 w/v %.

5. A liquid agent for a contact lens according to claim 1, which has a pH of from 5.0 to 9.0.

6. A liquid agent for a contact lens according to claim 1, which is an aqueous solution.

7. A liquid agent for a contact lens according to claim 1, wherein said carboxylated amine is selected from the group consisting of laurylaminopropionic acid, laurylaminodipropionic acid, octylaminopropionic acid, octylaminodipropionic acid, 2-octylaminopropionic acid, 2-octylaminodipropionic acid, nonylaminopropionic acid, nonylaminodipropionic acid, decylaminopropionic acid, decylaminodipropionic acid, undecylaminopropionic acid, undecylaminodipropionic acid and salts thereof.

8. A liquid agent for a contact lens according to claim 1, further containing, as a cleaning component, a surface active agent selected from the group consisting of anionic, cationic, amphoteric and nonionic surface active agents.

9. A liquid agent for a contact lens according to claim 1, further containing at least one disinfectant that is different from said carboxylated amine.

* * * * *